US008110533B1

(12) United States Patent
Tsaur

(10) Patent No.: US 8,110,533 B1
(45) Date of Patent: Feb. 7, 2012

(54) LIQUID SOAP COMPOSITIONS

(75) Inventor: Liang Sheng Tsaur, Norwood, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/891,879

(22) Filed: Sep. 28, 2010

(51) Int. Cl.
*A61K 7/50* (2006.01)

(52) U.S. Cl. ........ 510/130; 510/156; 510/424; 510/426; 510/481; 510/490

(58) Field of Classification Search ........................ None
See application file for complete search history.

(56) References Cited

U.S. PATENT DOCUMENTS

| | | | | |
|---|---|---|---|---|
| 4,486,328 A | | 12/1984 | Knott et al. | |
| 4,975,218 A | | 12/1990 | Rosser | |
| 5,147,574 A | | 9/1992 | MacGilp et al. | |
| 5,308,526 A | | 5/1994 | Dias et al. | |
| 5,312,559 A | | 5/1994 | Kacher et al. | |
| 5,767,059 A | | 6/1998 | Umemoto et al. | |
| 5,851,978 A | * | 12/1998 | Shana'a | 510/417 |
| 6,812,192 B2 | | 11/2004 | Ribery et al. | |
| 6,906,016 B1 | | 6/2005 | Tsaur | |
| 2005/0020461 A1 | | 1/2005 | Seki | |
| 2005/0220736 A1 | | 10/2005 | Polonka et al. | |

FOREIGN PATENT DOCUMENTS

| | | |
|---|---|---|
| GB | 2 351 979 | 1/2001 |
| WO | 95/13355 | 5/1995 |
| WO | 96/36313 | 11/1996 |
| WO | 97/27279 | 7/1997 |

OTHER PUBLICATIONS

Co-Pending Appln.—Yang et al., Filed Sep. 28, 2010, entitled : Fragranced Soap Compositions.

* cited by examiner

*Primary Examiner* — Necholus Ogden, Jr.
(74) *Attorney, Agent, or Firm* — Milton L. Honig

(57) ABSTRACT

A liquid cleansing composition is provided which includes from 5 to 25% by weight of a fatty acids mixture and from 30 to 90% by weight of water, wherein the fatty acids mixture is present in a weight amount greater than a total of all surfactants other than soap present in the composition. Further, the fatty acids mixture is 70-95% of lauric and myristic fatty acids in a weight ratio from 9:1 to 1:2, and 5-30% $C_{16}$-$C_{20}$ fatty acid, all by weight of the fatty acids mixture. Still further, 60-90 mole % of the fatty acids mixture is neutralized into soap.

9 Claims, No Drawings

LIQUID SOAP COMPOSITIONS

BACKGROUND OF THE INVENTION

1. Field of the Invention

The present invention relates to stable liquid personal skin and hair cleansing compositions based on fatty acid technology.

2. The Related Art

Soap has been a mainstay active for cleansers. Most toilet bars contain this surfactant. That is why they are called soap bars.

Beginning many decades ago synthetic detergents, known shorthand as syndets, have been replacing soap. Among the reasons are that many syndets are milder, foam better and are more stable in liquid formats. Partially a result of a relatively higher melting point, soap is ideal for semi-solids such as bars. Contrary in aqueous liquid formulas, there are structuring and stability problems.

In recent years sustainability of resources has become an issue. Syndets are often petroleum derivatives. Those syndets that are prepared from renewable resources need further reactive chemical processing such as sulfonation and/or alkoxylation. By contrast, soaps are generally obtained from renewable resources. They are neutralized fatty acid salts which through mild chemical processing are readily available from vegetable triglycerides. Relevant technology is found in the disclosures which follow.

GB 2 351 979 B (Arai et al) describes liquid cleansing compositions containing mixtures of alkali metal soaps, anionic surfactants and amphoteric/zwitterionic surfactants. The soap/synthetic surfactant liquid compositions were recognized to have problems with low temperature storage stability. They tend to freeze and thereby cannot be readily pumped from their containers. Isoprene glycol with dipropylene glycol were utilized to solve the problem.

WO 97/27279 (Hamada et al.) discloses a body soap incorporating polyoxyethylene alkyl ether sulfate to reduce stiff skinfeel attributed to the soap. A specific ratio of soap to alkyl ether sulfate is needed to overcome the problem.

WO 96/36313 (Chatfield et al.) relates to aqueous liquid cleansing compositions containing soaps. In this patent, short chain fatty acid ($C_{10}$ or less) is united with a long chain ($C_{14}$-$C_{22}$) fatty acid soap to obtain a skin mild liquid with good lather.

U.S. Pat. No. 4,975,218 (Rosser et al.) reports a single liquid phase clear aqueous soap composition containing ethoxylated nonionic surfactants to enhance mildness. Included in the composition are 10-50% of $C_{12}$-$C_{18}$ fatty acid soaps and 5-30% of $C_8$-$C_{22}$ fatty alcohol having 20 to 50 ethoxylate groups. Preferred mixtures of lauric acid to myristic acid are in a ratio of 1:1 to 1:4.

U.S. Pat. No. 4,486,328 (Knott et al.) describes a clear liquid shampoo containing a mixture of water-soluble $C_8$-$C_{18}$ fatty acid soap and a zwitterionic detergent. The latter is present in a major proportion, i.e. more than 60% of total fatty acid and zwitterionic detergent, to provide the shampoo with stability and clarity. The mole ratio of zwitterionic detergent (e.g. cocoamidopropyldimethyl betaine) to fatty acid ranges from 1.2:1 to 2.3:1. Liquid compositions containing low levels of zwitterionic detergent are cloudy and show phase separation during storage.

U.S. Pat. No. 5,147,574 (MacGilp et al.) discloses a stable dispersoidal liquid soap personal cleanser. The mixture contains 5-20% saturated higher fatty acid potassium soap and 3-18% of free fatty acids. The weight ratio of soap to free fatty acid is 1:0.5 to 1:1 equivalent to about 62.7% to 45.8% of neutralization of total fatty acids. Preferred fatty acids of the invention are those being fully saturated with low levels of lauric acid and high levels of palmitic and stearic acids.

U.S. Patent Application Publication No. 2005/0020461 A1 (Seki) concerns a cleansing composition containing 20-50% of fatty acids and fatty acid salt (soap) mixtures in which 50-80% have 16 or higher carbon atoms. The higher chain lengths are used to improve both mildness and storage stability. High levels of lauric and myristic acids are not preferred due to the after-cleansing tight skinfeel and poor storage stability.

U.S. Pat. No. 6,812,192 B2 (Ribery) reports a foaming liquid for cleansing or make-up removal. Compositions therein contain fatty acids with degree of neutralization between 50 and 100 weight %. The comparative examples show that liquid cleansers containing partially neutralized fatty acids are unstable. At least one non-betaine amphoteric surfactant and at least one sulphosuccinate-type anionic surfactant are required to achieve stability.

Although there is substantial technology reported in the liquid soap area, none of the references have truly achieved a skin mild system that has highly controlled phase and viscosity stability without necessity to depend on syndets.

SUMMARY OF THE INVENTION

A liquid cleansing composition is provided which includes:

- (i) from 5 to 25% by weight of the composition of a fatty acids mixture in which:
  - (a) from 70 to 95% by weight of the mixture of $C_{12}$ and $C_{14}$ fatty acids present in a relative weight ratio of 9:1 to 1:2;
  - (b) from 5 to 30% by weight of the mixture of $C_{16}$-$C_{20}$ fatty acids;
  - (c) from 60 to 90 mole % of the fatty acids mixture being neutralized to form soaps; and
- (ii) from 30 to 90% by weight of the composition of water; and wherein the fatty acids mixture is present in a weight amount greater than a total of all surfactants other than soap present in the composition.

DETAILED DESCRIPTION OF THE INVENTION

Now it has been found that a stable liquid soap composition can be achieved by selection of fatty acids, control of neutralization levels and appropriate manipulation of their concentrations. More specifically, the mole percentage of the fatty acid mixture that is neutralized should lie in a range from 60 to 90%, preferably from 65 to 85%, and more preferably from 68 to 80%. Bases used to neutralize the fatty acids may be metal hydroxides such as potassium or sodium hydroxide, organic amines such as mono-, di- or tri-ethanol amine, or ammonium hydroxide and mixtures thereof. Combinations of lauric acids ($C_{12}$) and myristic acid ($C_{14}$) constitute from 70 to 95%, preferably from 75 to 90% by weight of the fatty acids mixture. The weight ratio of lauric to myristic acid is in the range from 9:1 to 2:1, preferably 4:1 to 2:1, to provide good lather volume and lather creaminess to the liquid soap compositions. From 5 to 30% and preferably from 10 to 25% by weight of the fatty acids mixture is constituted of $C_{16}$-$C_{20}$ chain lengths. Syndets may be present but their total amounts by weight should be less than the total weight amount of the fatty acids mixture.

The fatty acids mixture of this invention may amount to 5 to 25%, and optimally from 8 to 18% by weight of the composition.

In this disclosure the term “fatty acids mixture” is used to include a sum of both free fatty acids and neutralized fatty acids (i.e. soaps) in the liquid composition. The term “fatty acids mixture weight” refers to the weight of the free fatty acid together with the neutralized fatty acid, the latter including the weight of the neutralizing cations.

Water will be present in the compositions in amounts from 30 to 90%, preferably from 50 to 85%, and optimally from 65 to 80% by weight.

Zwitterionic surfactants may be formulated into compositions of this invention. Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative zwitterionics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxpropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

The amount of zwitterionic surfactant used in the invention depends on the amount of the fatty acids mixture in the liquid composition. It should be at least 25 wt % but less than 100 wt % of the amount of the fatty acids mixture, preferably in the range of 35 to 95 wt % of the fatty acids mixture amount.

Anionic and/or nonionic surfactants may also be included in the compositions. Examples of anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof.

The anionic surfactant may be for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Nonionic surfactants which may be used include the reaction products of compounds having a hydrophobic group and a reactive hydrogen atom. Exemplative are alcohols, acids, amides or alkyl phenols reacted with alkylene oxides, especially ethylene oxide either alone or with propylene oxide. Specific nonionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Also useful are the alkyl polysaccharides.

Water soluble/dispersible polymers are an optional ingredient that is highly preferred to be included in the liquid composition of the invention. These polymers can be cationic, anionic, amphoteric or nonionic types with molecular weights higher than 100,000 Dalton. They are known to increase the viscosity and stability of liquid cleanser compositions, to enhance in-use and after-use skin sensory feels, and to enhance lather creaminess and lather stability. Amount of the polymers when present may range from 0.1 to 10% by weight of the composition.

Examples of water soluble/or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol®Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance® 3000, N-Hance® 3196, N-Hance® GPX 215 or N-Hance® GPX 196 from Hercules; synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24. Also suitable are high molecular weight polyethylene glycols such as Polyox® WSR-205 (PEG 14M), Polyox® WSR-N-60K (PEG 45), and Polyox® WSR-301 (PEG 90M).

Water-soluble skin benefit agents may optionally be formulated into the liquid compositions of the invention. A variety of water-soluble skin benefit agents can be used and the level can be from 0 to 50% but preferably from 1 to 30% by weight of the composition. These materials include, but are not limited to, polyhydroxy alcohols. Preferred water soluble skin benefit agents are glycerin, sorbitol and polyethylene glycol.

Water-insoluble skin benefit agents may also be formulated into the compositions as conditioners and moisturizers. Examples include silicone oils; hydrocarbons such as liquid paraffins, petrolatum, microcrystalline wax, and mineral oil; and vegetable triglycerides such as sunflowerseed and cottonseed oils.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatabilities between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions of the invention may further include 0 to 10% by weight of sequestering agents, such as tetra sodium ethylenediaminetetraacetate (EDTA), EHDP or mixtures; opacifiers and pearlizers such as ethylene glycol distearate, titanium dioxide or Lytron 621 (Styrene/Acrylate copolymer); all of which are useful in enhancing the appearance or properties of the product.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

EXAMPLES

All examples in Tables 1, 2 and 3 were prepared in a vessel by mixing water, Carbopol® Aqua SF1, fatty acids, ethylene glycol distearate and titanium dioxide (when present) at 70° to 75° C. for 15 to 30 minutes until all the fatty acids melted. Polyox® WSR 301 was predispersed in 25% sodium hydroxide solution. The predispersion was then added slowly to the charged vessel to neutralize the molten fatty acids and allowed to mix for 15 to 25 minutes at 70° to 75° C. Cocoamidopropyl betaine, sodium laureth(1) sulfate and other synthetic surfactants were then added and mixed at 70° to 75° C. for another 15 to 20 minutes. Subsequently, the mixture was cooled below 40° C. All the other ingredients such as preservatives and perfume were lastly charged to the vessel and mixed for 10 more minutes. Each resultant formula was aged overnight at room temperature (RT). Viscosity was measured using a Brookfield viscometer (20 rpm using #5 spindle for 30 seconds at 20° C.). The viscosity results are recorded in the Tables. Samples were then stored at 4° C. and 45° C. for stability evaluation. Physical stability of the samples after the storage test was visually assessed and viscosity was measured using the same method described above after the sample was aged at 20° to 25° C. room temperature for 20 to 24 hours. These results are also recorded in the Tables.

TABLE 1

Effect of co-surfactant level on liquid stability

| Example No. | 1 | 2 | 3 | 4 | 5 | — | — | — | — |
|---|---|---|---|---|---|---|---|---|---|
| Comparative Example | — | — | — | — | | A | B | C | D |
| Na cocoamidopropyl betaine | 7 | 7 | 3.5 | 5 | 7 | 7 | 10 | 12 | 12 |
| Na laurylethyl sulfate | 0 | 2 | 2 | 4 | 0 | 4 | 2 | 2 | 0 |
| Fatty acyl isethionate mixture[1] | — | — | — | — | 4 | — | — | — | — |
| Lauric acid | 7.6 | 7.6 | 7.6 | 7.6 | 7.6 | 7.6 | 7.6 | 7.6 | 7.6 |
| Myristic acid | 3 | 3 | 3 | 3 | 3 | 3 | 3 | 3 | 3 |
| Palmitic acid | 0.54 | 0.54 | 0.54 | 0.54 | 0 | 0.54 | 0.54 | 0.54 | 0.54 |
| Stearic acid | 0.56 | 0.56 | 0.56 | 0.56 | 0 | 0.56 | 0.56 | 0.56 | 0.56 |
| Ethylene glycol distearate | 1.0 | 1 | 1.0 | 1.0 | — | 1 | 1.0 | 1.0 | 1.0 |
| Titanium Dioxide | 0.1 | 0.1 | 0.1 | 0.1 | 0.02 | 0.1 | 0.1 | 0.1 | 0.1 |
| Carbopol ® Aqua SF1 | 0.9 | 0.9 | 0.9 | 0.9 | 0.8 | 0.9 | 0.9 | 0.9 | 0.9 |
| Polyox ® WSR 301 | — | 0.04 | — | 0.04 | 0.04 | 0.04 | — | — | — |
| Perfume | 1 | 1 | 1 | 1 | 1 | 1 | 1 | 1 | 1 |
| Sodium Hydroxide (25% in water) | 7.0 | 7.0 | 7.0 | 7.0 | 6.6 | 6.9 | 7.0 | 7.0 | 7.0 |
| pH | 8.23 | 8.25 | 8.51 | 8.30 | 8.23 | 7.90 | 8.04 | 7.90 | 7.89 |
| Total FA moles | 0.0551 | 0.0551 | 0.0551 | 0.0551 | — | 0.0551 | 0.0551 | 0.0551 | 0.0551 |
| NaOH (25% in water) to neut. aqua SF1 | 0.63 | 0.63 | 0.53 | 0.63 | — | 0.63 | 0.63 | 0.63 | 0.63 |
| NaOH (25% in water) to 100% neutralize Fatty acids mixture | 8.81 | 8.81 | 8.81 | 8.81 | — | 8.81 | 8.81 | 8.81 | 8.81 |
| Degree of fatty acid neutralization[2] | 72.3% | 72.3% | 72.3% | 72.3% | — | 72.3% | 72.3% | 72.3% | 71.9% |

TABLE 1-continued

| Storage Stability Results | | | | | | | | | |
|---|---|---|---|---|---|---|---|---|---|
| Initial viscosity (cps) overnight at RT | 4380 | 3200 | 1480 | 3200 | 26000 | 3600 | 4200 | 5040 | 3000 |
| Storage at RT for 4 weeks | 2900 | 2560 | 1300 | 2260 | 24800 | Separated[3] | Separated[3] | 3180 | 1920 |
| % Decrease in Viscosity at RT initial to 4 weeks | 34 | 20 | 12 | 29 | 5 | — | — | 37 | 36 |
| Storage at 4° C. for 1 week | 3580 | 2420 | 1440 | 2700 | 28000 | 4900 | 3700 | 4400 | 1660 |
| % Decrease in Viscosity at RT initial to 4° C. at 1 week | 18 | 24 | 3 | 16 | −1 | — | — | 13 | 45 |
| Storage at 45° C. for 2 weeks | 2880 | 2800 | 1200 | 2360 | 22000 | 2000 | 2600 | 2600 | 2000 |
| % Decrease in Viscosity at RT initial to 45° C. for 2 weeks | 34 | 13 | 19 | 26 | 15 | 44 | 38 | 48 | 33 |

[1]Contains 80% cocoyl isethionate and 20% stearic acid.

[2]Degree of fatty acid neutralization = (amount of NaOH added less amount of added NaOH required to neutralize SF1) divided by (amount of NaOH required to 100% neutralize fatty acids) as stated in mole terms.

[3]"Separated" means liquid shows separation with two or more phases at 45° C. storage condition.

Table 1 explores the effect of synthetic surfactant level on liquid stability. Five examples (1-5) of this invention were compared to four examples (A-D) outside the invention. In Examples 1 to 5 the total amount of synthetic surfactants is less than the total amount of fatty acids. All of the first five examples exhibited stability at all storage conditions, i.e., retaining at least 60%, preferably at least 66% and optimally at least 70% of the initial viscosity under all storage conditions. Comparative examples A to D containing total synthetic surfactants close to or higher than the total amount of the fatty acids mixture were not stable. They either showed phase separation at room temperature (see A and B) or did not retain 60% or more of their initial viscosity after storage at either 45° C. or 4° C.

TABLE 2

| Effect of degree of neutralization and fatty acids composition | | | | | | | | |
|---|---|---|---|---|---|---|---|---|
| Example No. | 6 | 7 | — | — | — | — | — | — |
| Comparative Example | — | — | E | F | G | H | I | J |
| Na cocoamidopropyl betaine | 7 | 7 | 7 | 7 | 7 | 7 | 7 | 7 |
| Na laurylethyl sulfate | 2 | 2 | 2 | 2 | 2 | 2 | 2 | 2 |
| Lauric acid (wt % of fatty acids mixture) | 7.6 (65.5%) | 6 (51.2%) | 7.6 (65.5%) | 11.7 (100%) | 6.7 (57.2%) | 4.7 (40.2%) | 3.4 (28.3%) | 0 (0%) |
| Myristic acid (wt % of fatty acids mixture) | 3 (25.6%) | 4.5 (39.3%) | 3 | 0 | 1.0 | 1 | 6.9 (57.7%) | 10.3 (85.7%) |
| Palmitic acid (wt % of fatty acids mixture) | 0.54 | 0.54 | 0.54 | 0 | 1.96 (16.7%) | 2.94 (25.1%) | 0.83 | 0.83 |
| Stearic acid (wt % of fatty acids mixture) | 0.56 | 0.56 | 0.56 | 0 | 2.04 (17.4%) | 3.06 (26.1%) | 0.87 | 0.87 |
| Ethylene glycol distearate | 1.0 | 1.0 | 1.0 | 1.0 | 1.0 | 1.0 | 1.0 | 1 |
| Carbopol ® Aqua SF1 | 0.9 | 0.45 | 0.9 | 0.9 | 0.9 | 0.9 | 0.9 | 0.45 |
| Polyox ® WSR 301 | 0.04 | 0.04 | 0.04 | 0.04 | 0.04 | 0.04 | 0.04 | 04.04 |
| Aqualon ® D4051 cationic guar | 0.05 | 0.05 | — | — | — | — | 0.05 | 0.05 |
| Glycerine | 2 | 2 | — | — | — | — | 2 | 2 |
| Perfume | 1 | 1 | 1 | 1 | 1 | 1 | 1 | 1 |
| NaOH (25% in water) | — | — | 6.0 | 7.0 | 7.0 | 7.0 | — | — |
| KOH (45% in water) | 6.3 | 5.9 | — | — | — | — | 2 | 2 |
| pH | 8.50 | 8.58 | 7.80 | 8.1 | 8.11 | 8.38 | 8.52 | 8.6 |

TABLE 2-continued

Effect of degree of neutralization and fatty acids composition

| | | | | | | | | |
|---|---|---|---|---|---|---|---|---|
| Amount of Alkali Hydroxide to neutralize SF1 | 0.49 | 0.25 | 0.63 | 0.63 | 0.63 | 0.63 | 0.49 | 0.25 |
| Total moles of fatty acids | 0.0551 | 0.0543 | 0.0551 | 0.0585 | 0.0527 | 0.050 | 0.0536 | 0.0515 |
| Amount of Alkali Hydroxide required to 100% neutralize fatty acids mixture | 6.85 | 6.75 | 8.81 | 9.36 | 8.44 | 8.02 | 6.66 | 6.40 |
| Degree of fatty acid neutralization[1] | 84.8% | 83.7% | 61.0% | 68.1% | 75.5% | 79.2% | 78.2% | 83.6% |
| Initial viscosity (cps) Overnight at RT | 19700 | 18000 | 13500 | 2500 | 6000 | Over 20000 | 126900 | Over 20000 |
| Storage at RT for 4 weeks | 19500 | 16700 | 13000 | 1100 | 2560 | gel | gel | gel |
| % Decrease in Viscosity at RT initial to 4 weeks | 1 | 7 | 4 | 56 | 57 | — | — | — |
| Storage at 4° C. for 1 week | 19500 | 16800 | 3800 | 2000 | 4600 | gel | 17500 | gel |
| % Decrease in Viscosity at RT initial to 4° C. at 1 week | 1 | 7 | 72 | 20 | 23 | — | −4 | — |
| Storage at 45° C. for 2 weeks | 19200 | 16400 | 10800 | 1600 | 2900 | 3600 | 10820 | 13000 |
| % Decrease in Viscosity at RT initial to 45° C. for 2 weeks | 3 | 9 | 30 | 36 | 52 | — | 36 | — |

[1]Degree of fatty acid neutralization = (amount of NaOH/KOH added) less (amount of NaOH/KOH required to neutralize SF1) divided by (amount NaOH/KOH required to 100% neutralize fatty acids) as stated in mole terms.

Table 2 explores the effect of fatty acid composition and the degree of neutralization on stability. Comparative examples E has the same composition as Example 2 of Table 1 except having lower degree of fatty acid neutralization, 61% vs.72.3%. Comparative example E has higher initial viscosity with lotion-like texture. However, the liquid turned thin after being stored at 4° C. for 1 week. Comparative examples F, G, H, I and J show the criticality of fatty acid composition on stability. Comparative Example F contains only lauric acid. Comparative Example G contains a high wt % of palmitic and stearic acids (34.1 wt % of total fatty acids). Example H contains 51.2 wt % of palmitic and stearic acids. Both G and H do not have enough of lauric and myristic acids to achieve stability.

Comparative Examples I and J contain too low a ratio of lauric acid to myristic acid (1:2.03 for Example 1 and 0:10.3 for Example J). Both have stability problems during storage at RT, 4° C. or 45° C.

These examples contain either a high wt % of C14 (Examples I and J) or too high of C16/C18 (Example G and H) and insufficient amounts of lauric acid. They became non-pourable gels after aging at room temperature over several weeks.

TABLE 3

Effect of neutralization and fatty acid composition on liquid stability

| Example No. | 7 | | 8 | 9 | | |
|---|---|---|---|---|---|---|
| Comparative Example | | K | | | L | M |
| Na cocoamido propyl betaine | 9 | 9 | 9 | 9 | 9 | 9 |
| Lauric acid | 7.6 | 7.6 | 7.6 | 7.6 | 7.6 | 11.7 |
| Myristic acid | 3 | 3 | 3 | 3 | 3 | 0 |
| Palmitic acid | 0.54 | 0.54 | 0.54 | 0.54 | 0.54 | 0 |
| Stearic acid | 0.56 | 0.56 | 0.56 | 0.56 | 0.56 | 0 |
| Titanium Dioxide | 0.1 | 0.1 | — | — | — | — |
| Carbopol ® Aqua SF1 | 0.9 | 0.6 | 1.2 | 1.2 | 1.2 | 1.2 |
| Polyox ® WSR 301 | 0.04 | 0.04 | — | — | — | — |
| NaOH (25% in water) | 6.8 | 6.0 | — | — | — | — |

TABLE 3-continued

| | | | | | | |
|---|---|---|---|---|---|---|
| KOH (45% in water) | — | — | 5.45 | 6.58 | 4.15 | 5.70 |
| Perfume | 1 | 1 | 1 | 1 | 1 | 1 |
| Total moles of fatty acids | 0.0551 | 0.0551 | 0.0551 | 0.0551 | 0.0551 | 0.0551 |
| Amount of Alkali Hydroxide required to 100% neutralize fatty acids | 8.81 | 8.81 | 5.83 | 5.83 | 5.83 | 7.25 |
| Amount of Alkali Hydroxide required to neutralize SF1 | 0.63 | 0.42 | 0.65 | 0.65 | 0.65 | 0.65 |
| Degree of fatty acid neutralization[1] | 70% | 63.3% | 70.3% | 90% | 51.2% | 69.7% |
| pH | 9.09 | 7.94 | 8.14 | 8.83 | 7.45 | 8.08 |
| Storage Stability Result | | | | | | |
| Initial viscosity (cps) Overnight at RT | 2500 | 12780 | 4800 | 13500 | 12700 | 6600 |
| Storage at RT for 4 weeks | 2160 | 2200 | 4000 | 11200 | 14900 | Over 20000 |
| % Decrease in Viscosity at RT initial to 4 weeks | 14 | 83 | 17 | 17 | −17 | — |
| Storage at 4° C. for 1 week | 2360 | 2000 | 3840 | 11740 | 6300 | 13200 |
| % Decrease in Viscosity at RT initial to 4° C. for 1 week | 6 | 84 | 20 | 13 | 50 | −100 |
| Storage at 45° C. for 2 weeks | 2180 | 9940 | 3300 | 10200 | 13300 | 2620 |
| % Decrease Viscosity at RT initial to 45° C. for 2 weeks | 13 | 22 | 31 | 24 | −5 | 60 |

[1]Degree of fatty acid neutralization = (amount of NaOH/KOH added) less (amount of NaOH/KOH required to neutralize SF1) divided by (amount NaOH/KOH required to 100% neutralize fatty acids) as stated in mole terms.

Three more examples of this invention and 3 comparative examples with similar synthetic surfactant and fatty acids compositions were prepared and detailed in Table 3. These examples further confirm that both the degree of fatty acid neutralization and fatty acid composition are critical to the liquid stability of this invention. To make liquid compositions of this invention stable at all storage conditions, degree of fatty acid neutralization should be more than 60%, preferably at least 65% and it should contain both short chain and long chain fatty acids in the composition.

What is claimed is:

1. A liquid cleansing composition comprising:

(i) from 5 to 25% by weight of the composition of a fatty acids mixture comprising:

(a) from 70 to 95% by weight of the mixture of $C_{12}$ and $C_{14}$ fatty acids present in a relative weight ratio of 4:1 to 2:1;

(b) from 5 to 30% by weight of the mixture of $C_{16}$-$C_{20}$ fatty acids;

(c) from 65 to 90 mole % of the fatty acids mixture being neutralized to form soaps; and (ii) from 30 to 90% by weight of the composition of water; and wherein the fatty acids mixture is present in a weight amount greater than a total of all surfactants other than soap present in the composition.

2. The composition according to claim 1 further comprising zwitterionic surfactants in an amount from 2 to 25% by weight of the composition.

3. The composition according to claim 2 wherein the zwitterionic surfactants total 25 to less than 100% by weight relative to the weight of the fatty acids mixture.

4. The composition according to claim 2 wherein the zwitterionic surfactants total 35 to 95% by weight relative to the weight of the fatty acids mixture.

5. The composition according to claim 2 further comprising from 0 to 10% by weight of the composition of surfactants selected from anionic, nonionic and surfactant mixtures thereof, and wherein the total zwitterionic surfactants are in amounts greater than the total anionic and nonionic surfactants.

6. The composition according to claim 1 further comprising from 0.1 to 10% by weight of the composition of water soluble or water swellable polymers.

7. The composition according to claim 1 which retains at least 70% of initial viscosity after storage at 20° C. for 4 weeks.

8. The composition according to claim 1 wherein from 65 to 85 mole % of the fatty acids mixture is neutralized to form soaps.

9. The composition according to claim 1 wherein the mixture of $C_{16}$-$C_{20}$ fatty acids ranges from 5 to 25% by weight of the mixture.

* * * * *